United States Patent [19]
Liu

[11] Patent Number: 5,931,813
[45] Date of Patent: Aug. 3, 1999

[54] RETRACTABLE AND DESTRUCTIBLE SAFETY SYRINGE

[76] Inventor: Wen-Neng Liu, 5th Floor—2, No. 200, Section 1, Tun-Hua S. Road, Taipei, Taiwan

[21] Appl. No.: 08/998,495

[22] Filed: Dec. 26, 1997

[51] Int. Cl.⁶ ........................................... A61M 5/00
[52] U.S. Cl. .......................... 604/110; 604/195; 604/220
[58] Field of Search ..................................... 604/110, 192, 604/187, 195, 263, 218, 220

[56] References Cited

U.S. PATENT DOCUMENTS

| | | |
|---|---|---|
| 4,804,370 | 2/1989 | Haber et al. . |
| 4,898,589 | 2/1990 | Dolgin et al. . |
| 4,950,241 | 8/1990 | Ranford . |
| 5,205,824 | 4/1993 | Mazur . |
| 5,242,402 | 9/1993 | Chen . |
| 5,364,359 | 11/1994 | Van den Haak . |
| 5,370,619 | 12/1994 | Rossi . |
| 5,378,240 | 1/1995 | Curie et al. . |
| 5,395,346 | 3/1995 | Maggioni . |
| 5,415,638 | 5/1995 | Novacek et al. . |
| 5,533,975 | 7/1996 | Lu . |

FOREIGN PATENT DOCUMENTS

WO 92/11883  7/1992  European Pat. Off. .
WO 92/18186  10/1992  European Pat. Off. .

*Primary Examiner*—John D. Yasko
*Attorney, Agent, or Firm*—Ladas & Parry

[57] ABSTRACT

A retractable and destructible safety syringe including a syringe barrel, a plunger, a needle holder, a needle, capture elements formed on the needle holder or the plunger and a one-way movable detent formed on the plunger or the needle holder. When a piston of the plunger is fully depressed within the syringe barrel, the detent can be easily firmly engaged with the capture elements, whereby the needle holder and the needle can be together pulled back into the barrel. In addition, when the fully retracted plunger is depressed again, the tip of the needle is pressed against a shoulder section of the barrel, being bent and destroyed thereby. Sealing fixing rings are formed on outer wall of the needle holder and inner wall of the needle holder cavity, serving to sealably and separably engage the needle holder with the needle holder cavity. A latch plate is disposed between the barrel and the plunger to prevent the plunger from being pushed to latch the capture elements to the detent by mistake.

26 Claims, 11 Drawing Sheets

RETRACTABLE AND DESTRUCTIBLE SAFETY SYRINGE

BACKGROUND OF THE INVENTION

The present invention relates to a retractable and destructible safety syringe which has a simple structure and which can be easily manufactured at low cost and commercialized.

Various types of disposable syringes are currently widely used. After being discarded, large amounts of such syringes result in pollution problems. The used syringes often injure medical personnel and infect the personnel with viruses or bacteria carried by patients who have earlier used the syringes. In particular, a serious danger presented to medical personnel and others handing used syringes is exposure to the AIDS virus.

In order to solve the above-mentioned problems, various types of retractable syringes have been developed. For example, in one syringe type, a spring is installed between the syringe barrel and the piston for pulling the needle back into the barrel after injection. However, due to the properties of the medications held within the syringe barrel and as a result of safety requirements, the materials which may be used to manufacture the spring are strictly limited. Therefore, the structure of such a syringe is complicated and the manufacturing cost is very high. Various types of safety syringes free from the springs just described have been also developed. In such syringes, a latch member is disposed at the bottom of the syringe barrel, whereby when the plunger is pushed to the bottom of the barrel, the latch member latches the plunger to the needle. Then, when the plunger is pulled back, the needle is retracted into the barrel along with the plunger so as to avoid risk of injury from the needle to medical personnel and others handling the syringe.

In order to avoid leakage of the liquid medicine within the syringe and to avoid unexpected disconnection of the needle from the barrel, the needle must be firmly attached to the barrel. However, if the needle is too firmly attached to the barrel, it will be difficult to pull the needle back into the barrel. Therefore, the manner in which the needle is attached to the syringe barrel presents a challenging design problem.

In addition, in the case where it is necessary to securely latch the plunger with the needle, firm engagement required for secure latching presents another design difficulty. Conversely, designs in which the plunger and needle easily latch together often provide unreliable engagement, resulting in latching which is insufficient to pull the needle back into the barrel. Therefore, a reliable assembly to latch the plunger with the needle also presents a challenging design problem.

Moreover, in conventional syringe designs employing a retractable needle as described above, it often occurs that before the injection is completed, the plunger is latched with the needle by mistake. This leads to waste of the needle and syringe.

SUMMARY OF THE INVENTION

It is therefore a primary object of the present invention to provide a retractable and destructible safety syringe which is free from leakage and has a needle which does not become accidentally detached from the barrel and which can be easily retracted into the barrel.

It is a further object of the present invention to provide a safety syringe in which the plunger can easily be firmly latched to the needle while still being reliably retractable into the barrel.

It is still a further object of the present invention to provide a safety syringe in which before the injection is complete, the needle is prevented from being latched by mistake.

According to the above objects, the retractable and destructible safety syringe of the present invention includes: a syringe barrel having a first end and a second end and being formed with an internal chamber, the first end being disposed with a needle socket defining a needle holder cavity, an annular shoulder section being formed between the internal chamber and the cavity; a plunger having a first end and a second end, the first end being disposed with a piston and being fitted into the barrel, the plunger also having an axis; a needle holder having a first end and a second end, an outer periphery of the second end being fitted in the internal chamber of the first end of the barrel, the needle holder having an axis; a needle inserted into the first end of the needle holder; and a needle retracting means including: a capture element and a detent, the capture element having a first end and a second end, the first end being rotatably disposed on the first end of the plunger when the capture element is engaged with the detent, a distance between the first end of the capture element and either of the plunger or needle holder axes being defined as a first distance, the second end of the capture element extending toward the first end of the needle holder, a distance between the second end of the capture element and either of the plunger or needle axes (when the detent and the capture element are not engaged) being defined as a second distance, the second distance being less than the first distance; the detent having a first end and a second end, the first end of the detent being disposed on the first end of the plunger, the second end of the detent extending along the axis of the plunger toward the capture element and being disposed with a hook section having a radially extending hook surface, whereby when the first end of the plunger is pushed toward the first end of the barrel, the hook section of the detent slides into the second end of the capture element and when the plunger is pulled from the first end of the barrel to the second end thereof, the hook surface of the hook section abuts against the second end of the capture element to force the second end of the capture element toward the center of the detent so as to firmly engage with the hook surface of the hook section and to pull the needle holder and the needle back into the barrel.

At least two capture element arms are radially arranged about the axes. An alternative tubular-shaped capture element may be employed.

Either the inner walls of the needle holder cavity or the outer wall of the needle holder, or both the inner walls of the needle holder cavity and the outer wall of the needle holder further includes a sealing fixing ring.

At least two sealing fixing rings are provided.

The safety syringe further includes: a latch plate having a first end and a second end, the first end being connected with the second end of the barrel; a first latch section disposed at the second end of the latch plate; and a second latch section disposed at the second end of the plunger, the second latch section being latched with the first latch section so as to locate the detent near the capture element and to prevent the detent from engaging with the capture element by mistake.

The present invention can be best understood through the following description and accompanying drawings, wherein:

DETAILED DESCRIPTION OF THE PREFERRED EMBODIMENTS

With reference to FIGS. 1–4, the safety syringe 20 of a preferred embodiment of the present invention includes a syringe barrel 21, a plunger 22, a needle holder 23 and a needle 24. Syringe barrel 21 has a first end 28 and a second end 29, and is formed with an internal chamber 27. The first end 28 of syringe barrel 21 is disposed with a needle socket 30 defining a needle holder cavity 31. An annular shoulder section 33 is formed between the internal chamber 27 and the cavity 31 of syringe barrel 21. Plunger 22 has a first end 34 and a second end 35. The first end 34 of plunger 22 is fitted with a piston 36 and is fitted into barrel 21. Plunger 22 also has an axis 47. Needle holder 23 has a first end 37 and a second end 38. The outer periphery of the second end 38 of needle holder 23 is fitted in the internal chamber 27 of the first end 28 of barrel 21. Needle holder 23 has an axis 48. Needle 24 is inserted into the first end 37 of the needle holder 23.

Referring to FIGS. 3 to 9, the needle retracting means includes a capture element 25 and a detent 26. The capture element 25 extends from the second end 38 of needle holder 23. Capture element 25 has a first end 49 and a second end 50. As can best be seen in FIGS. 7 and 9, when capture element 25 is engaged with detent 26, the first end 49 of capture element 25 is rotatably disposed near the first end 34 of plunger 22 (to which detent 26 is attached). The distance 51 between the first end 49 of capture element 25 and axes 47, 48 is indicated at 51. The second end 50 of the capture element 25 extends radially toward axis 48 and first end 37 of needle holder 23. The distance 52 between the second end 50 of capture element 25 and axes 47, 48 is indicated at 52. Distance 51 is greater than distance 52.

Referring to FIGS. 3 to 14, detent 26 has a first end 53 and a second end 54. The first end 53 of detent 26 is attached to or integral with first end 34 of plunger 22. Detent 26 extends along axis 47 away from first end 34 of plunger 22 and toward capture element 25 (see FIG. 4). The second end 54 of detent 26 is disposed with a hook section 55 having a radially extending hook surface 56. When the first end 34 of plunger 22 is pushed to the first end 28 of barrel 21, hook section 55 of detent 26 slides into and through the second end 50 of capture element 25. When plunger 22 is then pulled from the first end 28 of barrel 21 to the second end 29 thereof, hook surface 56 of hook section 55 abuts against the second end 50 of capture element 25 to force the second end 50 toward the center of detent 26 in a direction shown by the arrow 57 in FIG. 9. This action firmly engages capture element 25 with hook surface 56 of hook section 55, whereby needle holder 23 and needle 24 can be together pulled into barrel 21.

Figure 2:
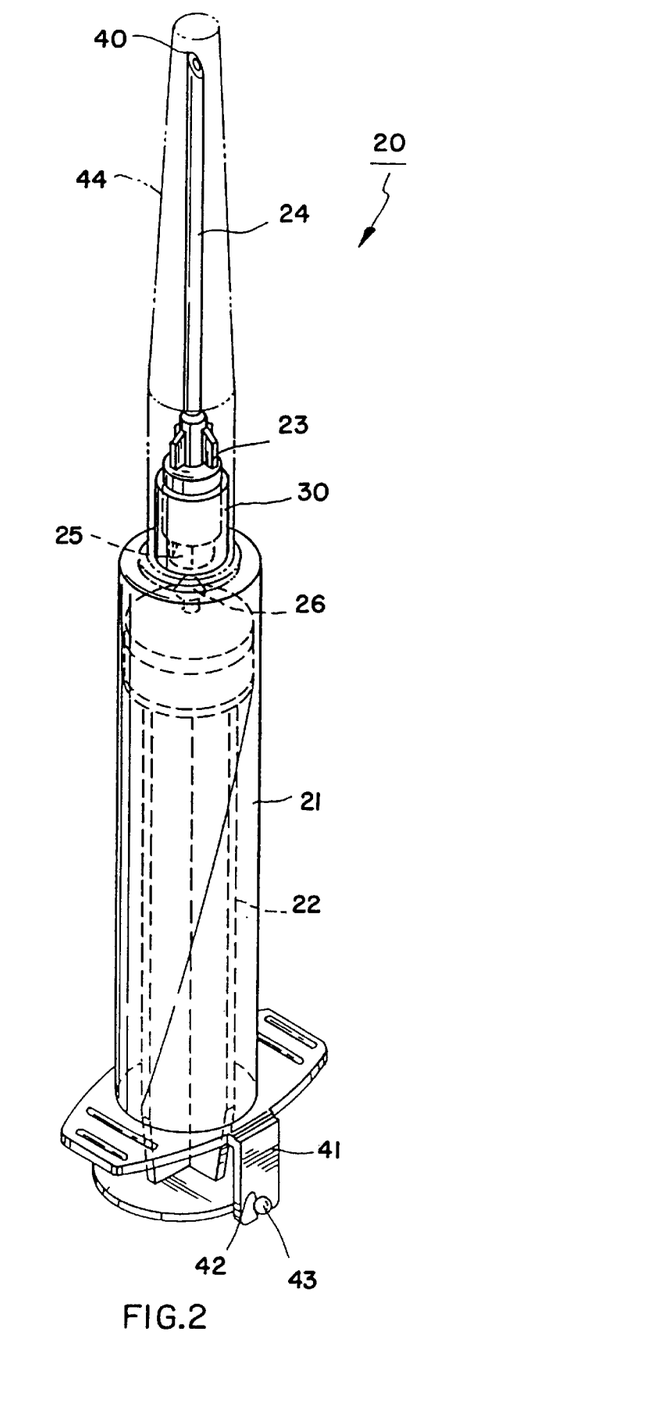
FIG. 2 is a perspective assembled view of the first embodiment of the present invention shown in FIG. 1.
Figure 3:
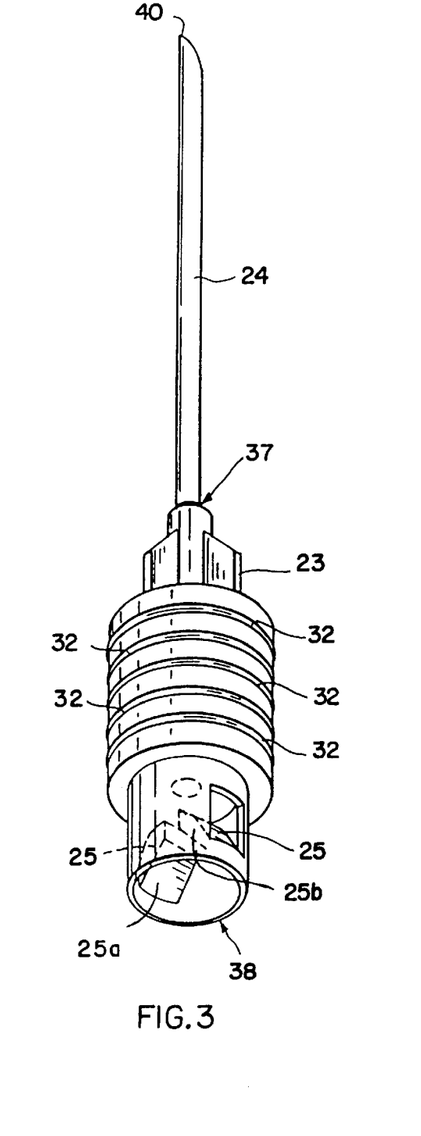
FIG. 3 is a perspective bottom view showing the needle and the needle holder of the first embodiment.

Referring to FIGS. 3 to 9, and particularly to FIG. 3, capture element 25 of syringe 20 comprises two arms 25a and 25b, which are disposed radially about axis 48. Any other number of arms may alternately be used to achieve the same capturing effect as arms 25a and 25b Referring to FIGS. 1 to 9, either the inner wall of needle holder cavity 31 of barrel 21 or the outer wall of needle holder 23 includes one or more sealing fixing rings 32. Sealing fixing rings 32 provide a snug fit between needle holder 23 and the inner walls of needle holder cavity 31, insuring that medication within syringe 20 does not leak out, and that needle holder 23 does not accidentally slip out of needle holder cavity 31. However, the fit between needle holder 23 and inner walls of needle holder cavity 31 is not so tight as to prevent needle holder 23 from being pulled into internal chamber 27 when capture element 25 and detent 26 are engaged and the user pulls plunger 22.

Figure 15:
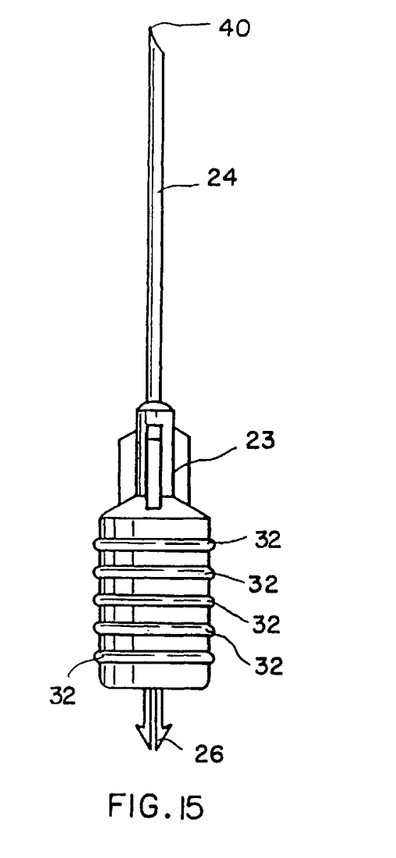
FIG. 15 is a front view of the needle and the needle holder of a third embodiment of the present invention.
Figure 16:
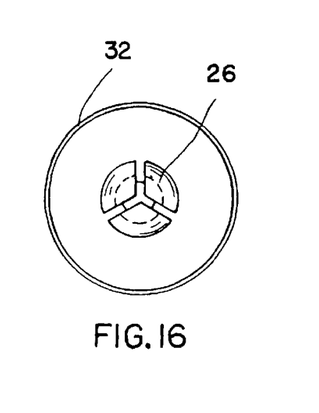
FIG. 16 is an enlarged bottom view of the needle and the needle holder of the third embodiment.
Figure 17:
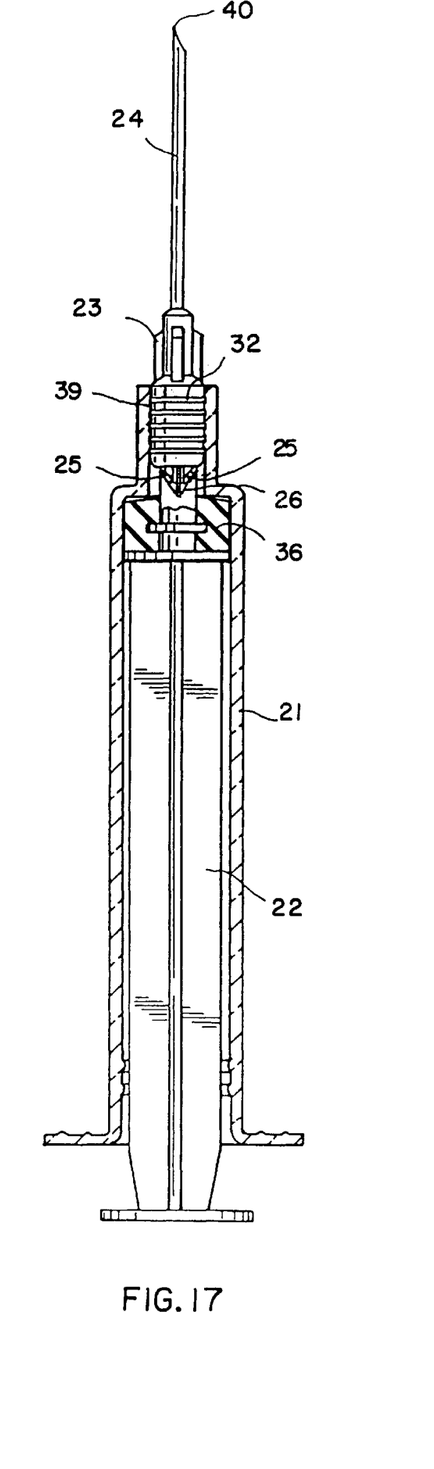
FIG. 17 is a sectional view according to FIG. 15, showing the syringe after liquid medicine has been completely injected and the capture element disposed on the plunger has been latched with the detent disposed on the needle holder.
Figure 18:
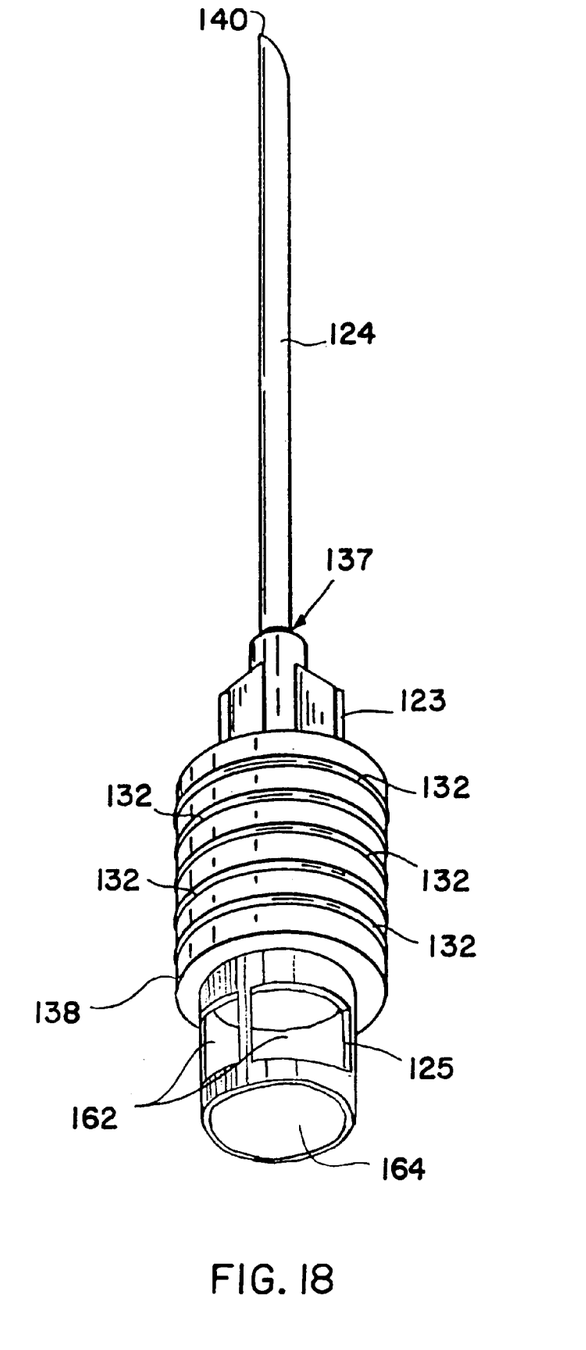
FIG. 18 is a perspective bottom view showing the needle and the needle holder of a fourth embodiment of the present invention.

In a third an alternative sealing fixing ring arrangement (the third embodiment of the present invention) shown in FIGS. 15 to 17, both the inner walls of needle holder cavity 31 of barrel 21 and the outer wall of needle holder 23 are provided with one or more sealing fixing rings 32, 39 fitted with each other. The fit between needle holder 23 and the inner walls of needle holder cavity 31 are as described above with reference to the first embodiment of the present invention shown FIGS. 1–9.

Figure 1:
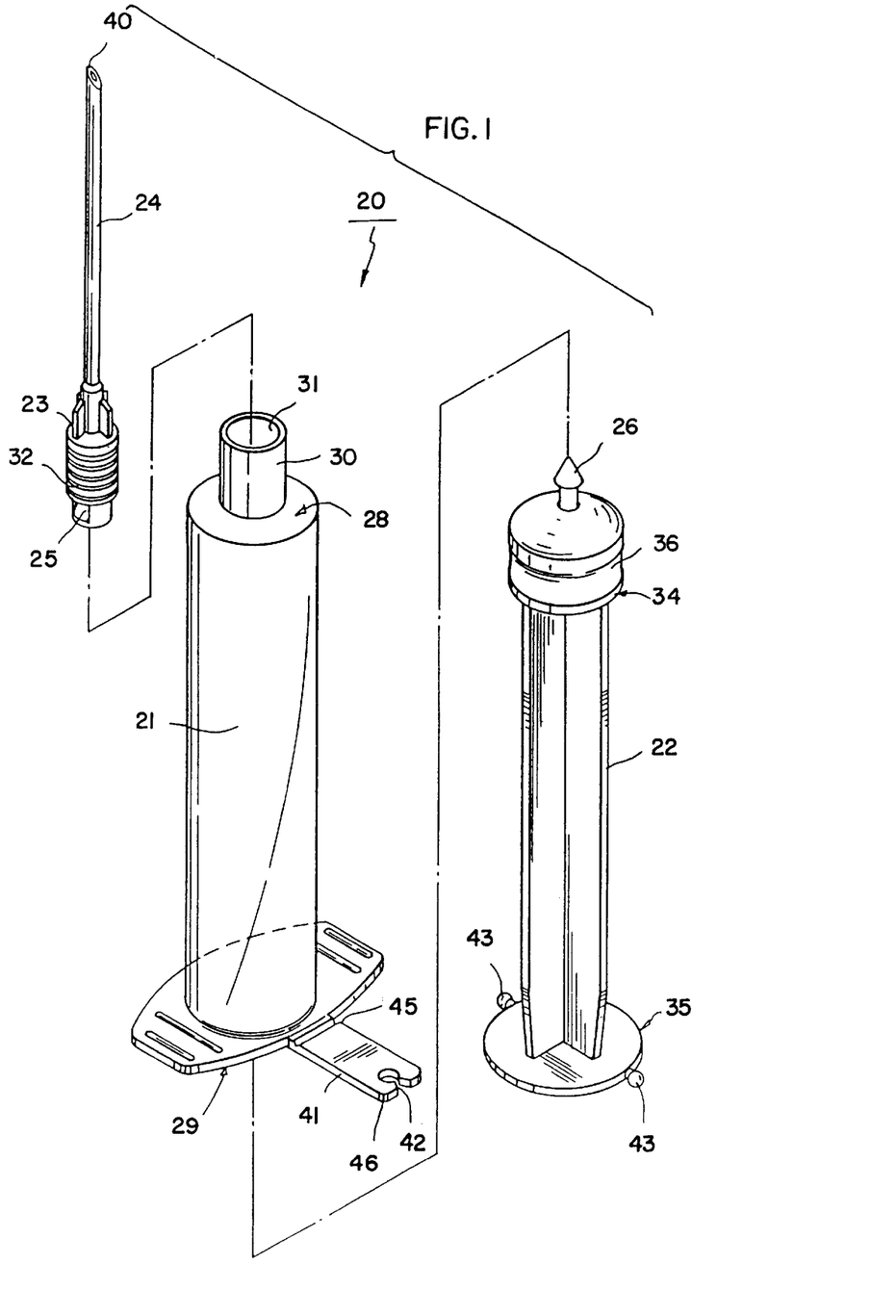
FIG. 1 is a perspective exploded view of a first embodiment of the present invention.

Referring to FIGS. 1 and 2, the safety syringe 20 of the present invention further includes a latch plate 41, a first latch section 42 and a second latch section 43. Latch plate 41 has first end 45 and a second end 46. The first end 45 of latch plate 41 is connected to the second end 29 of barrel 21. The first latch section 42 is disposed at the second end 46 of latch plate 41. The second latch section 43 is disposed at the second end 35 of plunger 22. The second latch section 43 can be latched to the first latch section 42 so as to locate detent 26 near capture element 25 and to prevent detent 26 from engaging with capture element 25 by mistake.

As shown in FIGS. 1 to 4, prior to use, needle holder 23 (with needle 24 attached thereto) is installed in needle holder cavity 31 of needle socket 30. Sealing fixing ring 32 of needle holder 23 is tightly and firmly fit against the inner wall of needle holder cavity 31. A needle sheath 44 is fitted around needle 24. Plunger 22 and piston 36 are fitted into internal chamber 27 of barrel 21. With particular reference to FIG. 2, the first latch section 42 of latch plate 41 is latched to the second latch section 43 of the second end 35 of plunger 22. Detent 26 is close to but separated from capture element 25.

Figure 9:
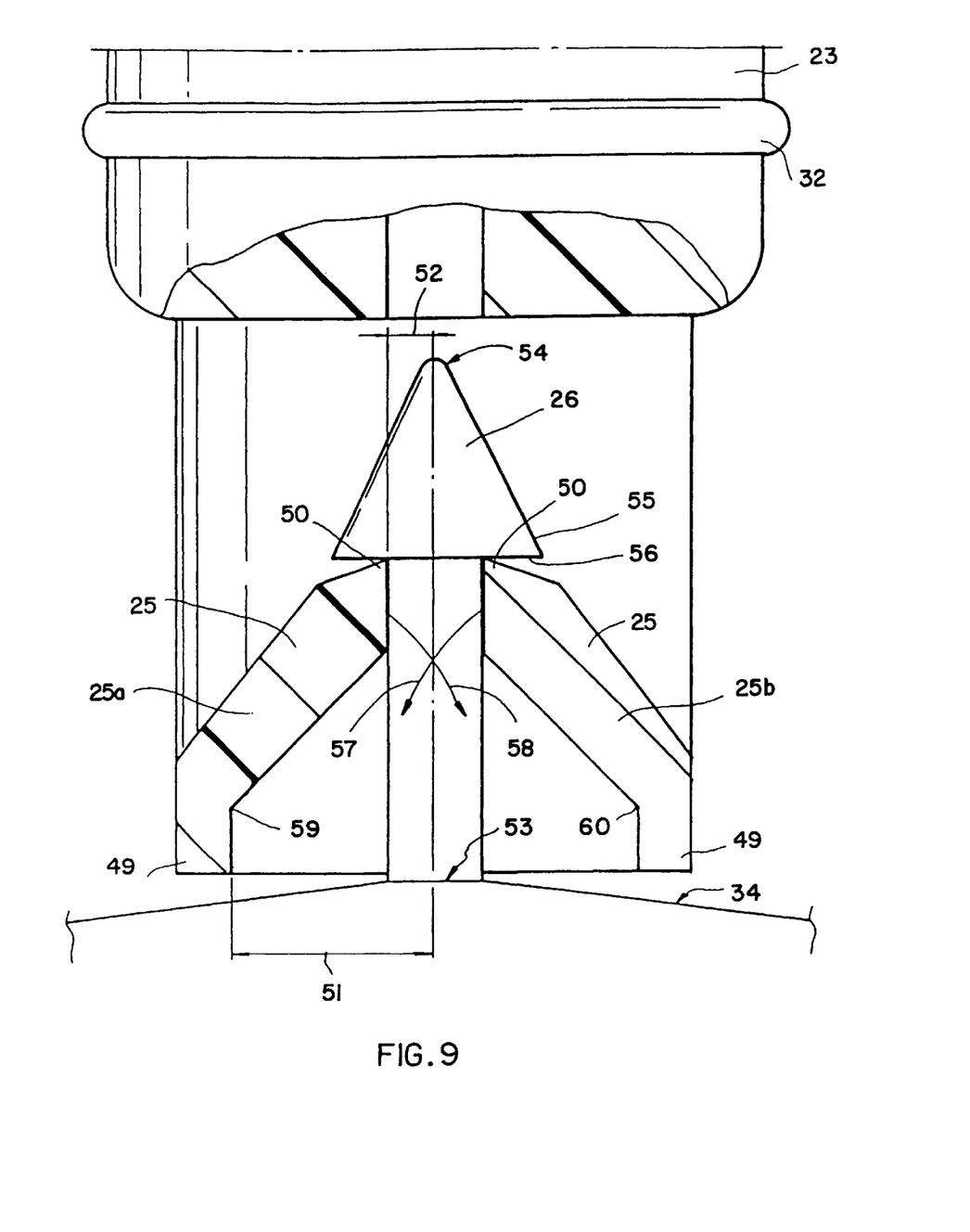
FIG. 9 is an enlarged view of area 9 denoted by phantom lines in FIG. 7, in which the plunger is pulled downward and the arms of capture element simultaneously clip the detent.
Figure 10:
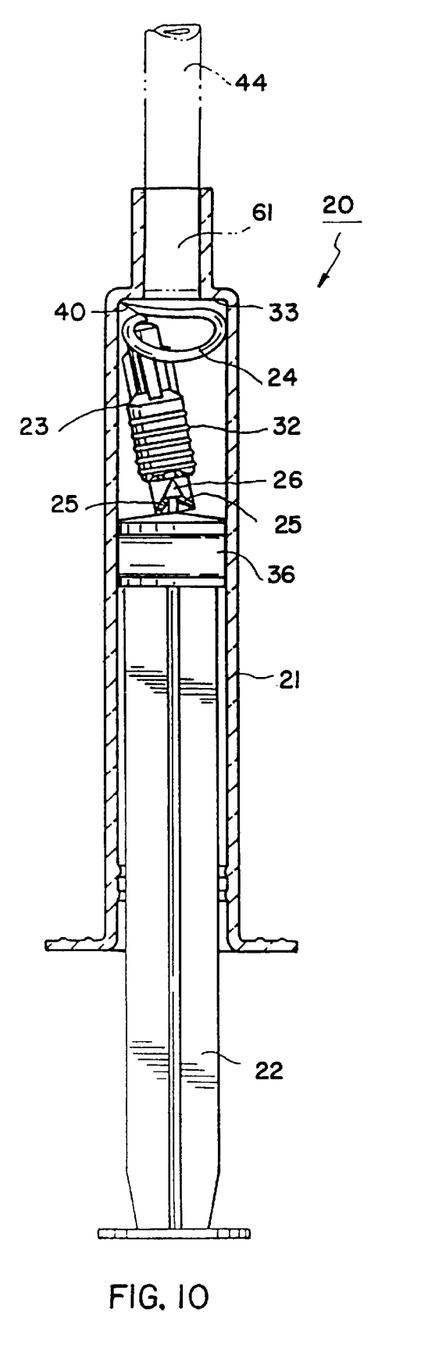
FIG. 10 is a sectional view showing the syringe after the needle has been retracted into the barrel, the plunger having again been pushed forward to bend and damage the needle.
Figure 11:
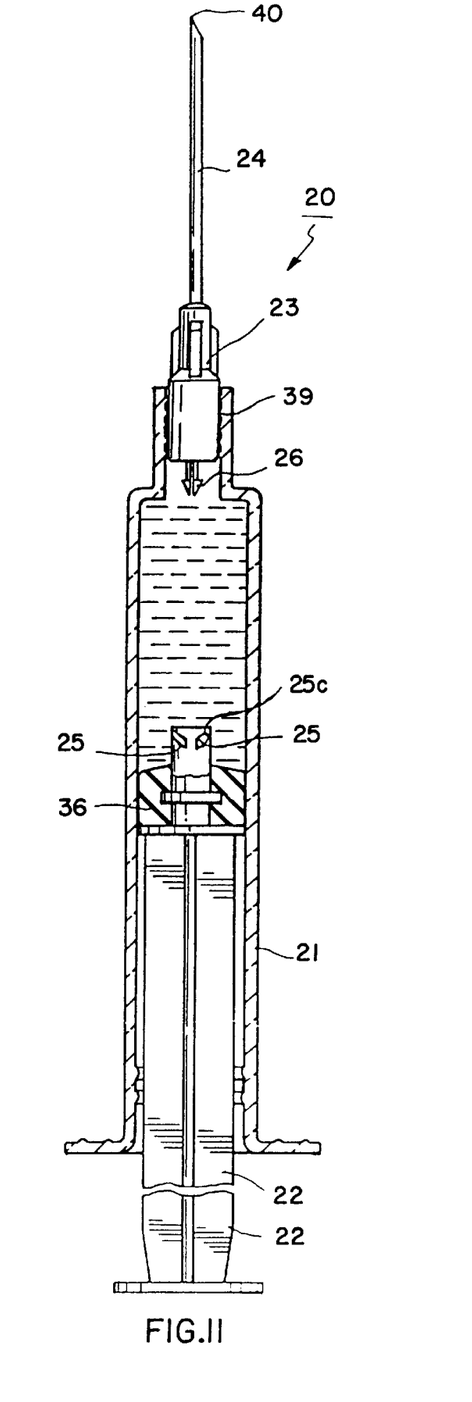
FIG. 11 is a sectional view of a second embodiment of the present invention, showing the liquid medicine sucked into the barrel.
Figure 12:
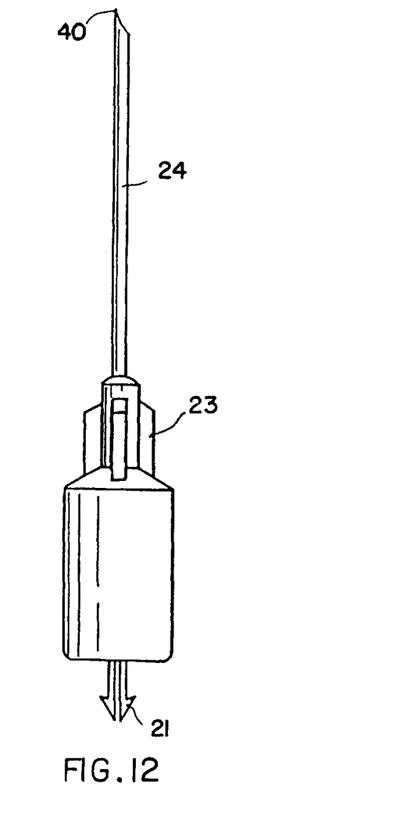
FIG. 12 is a front view of the needle and the needle holder of the second embodiment.
Figure 13:
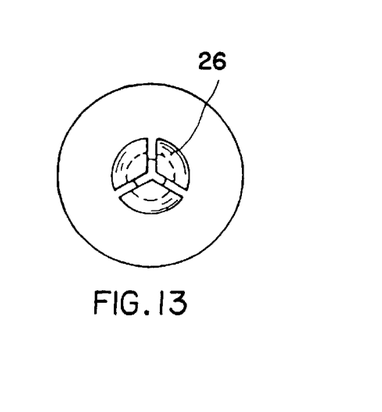
FIG. 13 is an enlarged bottom view of the needle and the needle holder of the second embodiment.
Figure 14:
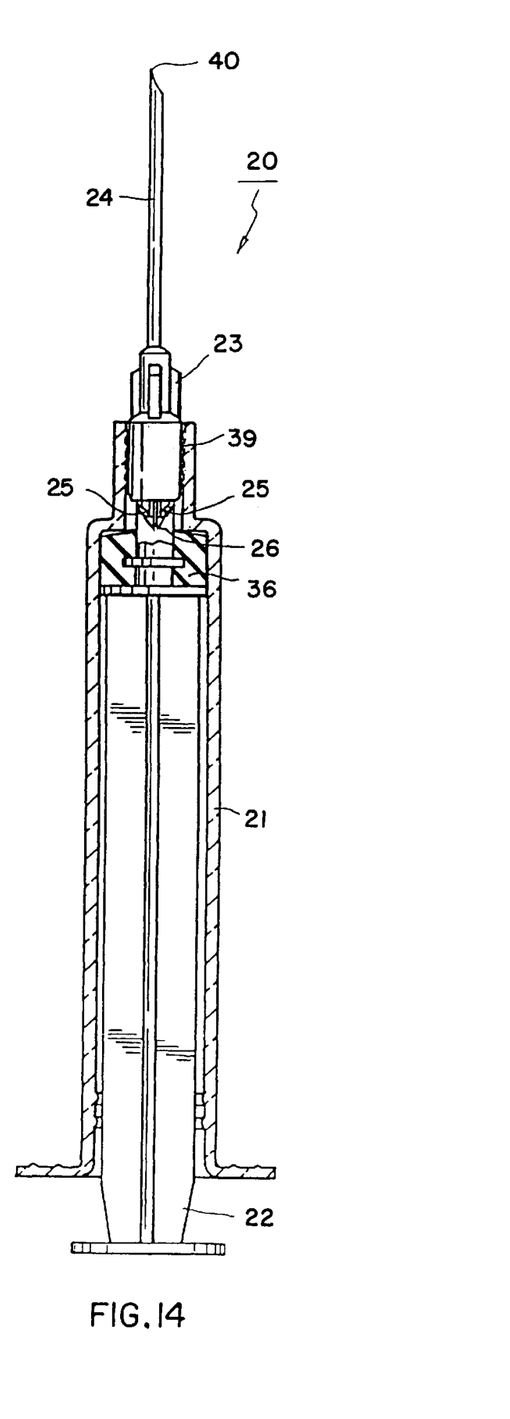
FIG. 14 is a sectional view according to FIG. 12, showing the syringe after liquid medicine has been completely injected and the capture element disposed on the plunger has been latched with the detent disposed on the needle holder.

To insure that needle 24 remains within barrel 21 once needle holder 23 and needle 24 have been retracted into internal chamber 27 (i.e., after the syringe has been used), capture element 25 is loosely engaged with detent 26 so that after tip 40 of needle 24 is pulled back into barrel 21, tip 40 will laterally tilt due to the unstable seating of capture element 25 on detent 26. In this regard, notice in FIG. 9 the clearance between first end 34 of plunger 22 and first end 49 of capture element 25 when detent 26 is engaged with capture element 25. This clearance causes needle 24 and needle holder 23 to tilt once needle 24 is fully retracted into barrel 21. Once tilted, tip 40 is positioned under shoulder section 33 of barrel 21. Shoulder section 33 serves to stop tip 40 when plunger 22 is then pushed by the user. This action by the user will therefore bend needle 24 (as shown in FIG. 10).

Figure 4:
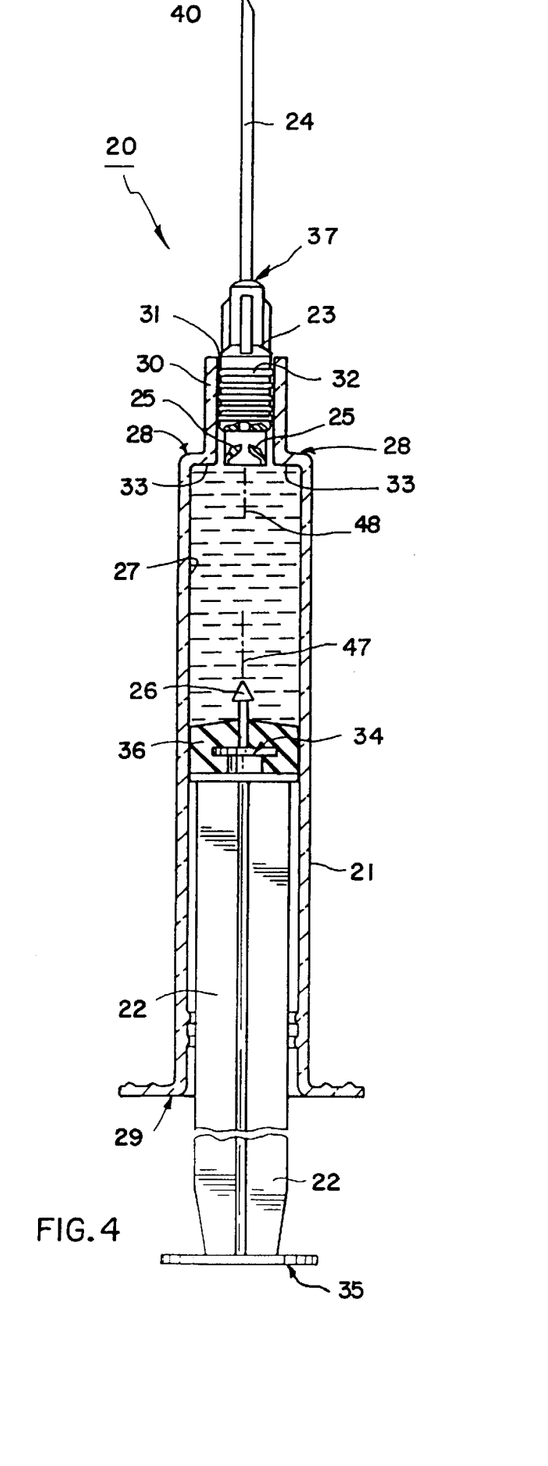
FIG. 4 is a sectional view showing liquid medicine sucked into the syringe barrel of the first embodiment.
Figure 5:
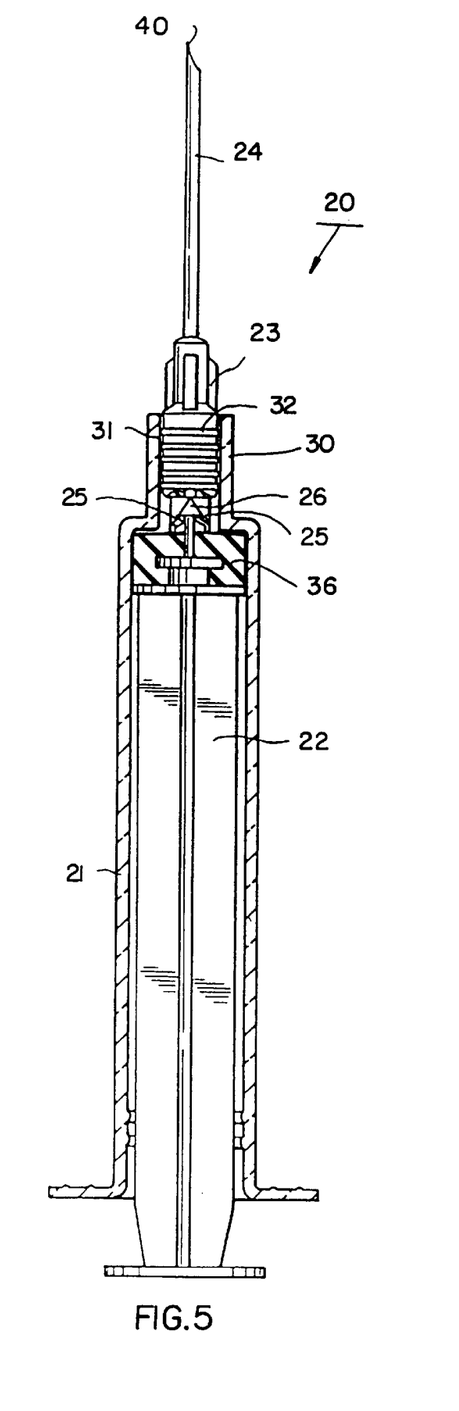
FIG. 5 is a sectional view showing liquid medicine after being completely injected, with the detent disposed on the piston being latched with the capture element disposed on the needle holder.
Figure 6:
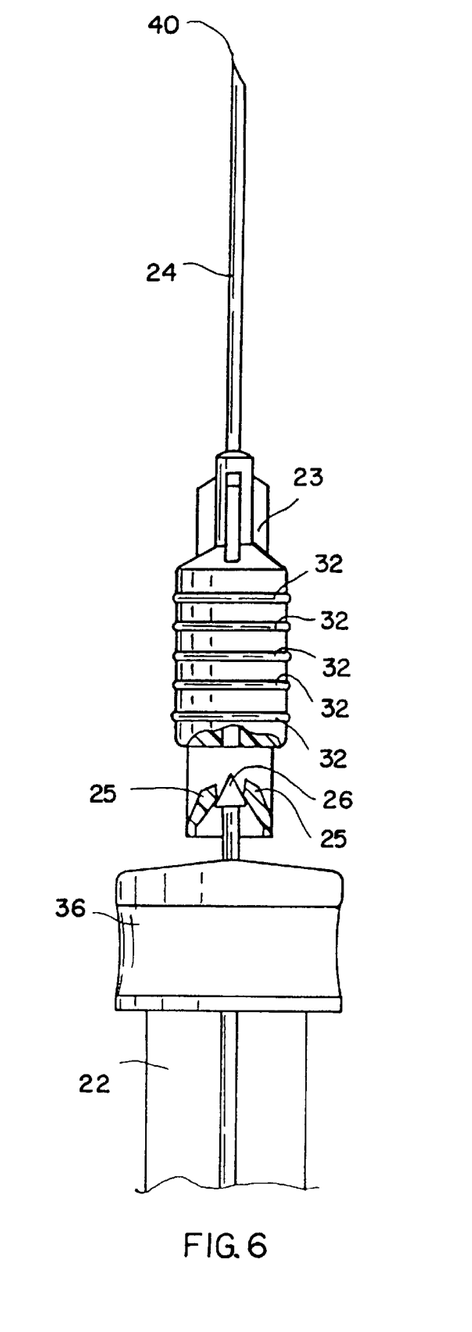
FIG. 6 is a front view showing the syringe when the liquid medicine is about to be completely injected and the detent is passing through the capture element.
Figure 7:
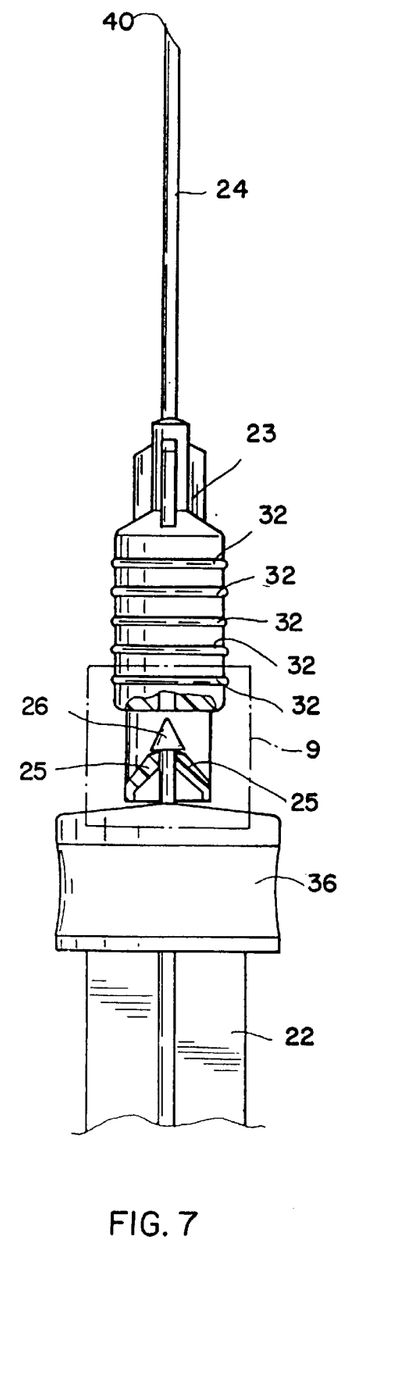
FIG. 7 is a front view showing the syringe when the detent has passed through the capture element and is gripped thereby.
Figure 8:
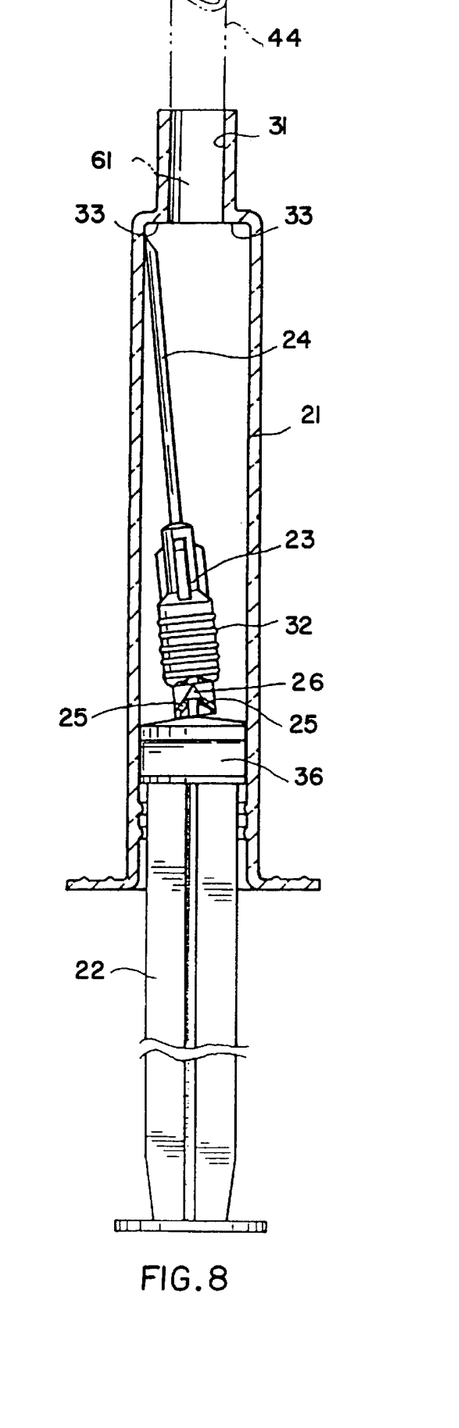
FIG. 8 is a sectional view showing the syringe when the injection has been completed and the needle has been pulled back into the barrel and automatically tilted.

When injecting, an operator thrusts needle 24 into a liquid medicine bottle. Then, latch plate 41 is unlatched, permitting plunger 22 to be pulled outward to suck the liquid medicine into barrel 21 (as shown in FIG. 4). Then, needle 24 is directed upward and plunger 22 is slightly pushed upward to exhaust the air trapped on the upper portion of barrel 21 from the tip 40 of needle 24. After the injection is completed, as shown in FIGS. 5 and 9, plunger 22 is pushed to its fully inserted position. At this time, detent 26 can easily push arms 25a and 25b of capture element 25 apart, thereby automatically engaging the capture element 25 of needle holder 23 with detent 26. Then, as shown in FIGS. 8 and 9, when plunger 22 is pulled back, arms 25a and 25b of capture element 25 are depressed by hook surface 56 of detent 26 and are respectively rotated about sections 59, 60 of capture element 25 in the direction shown by arrow 58 (see FIG. 9). This rotation of capture element arms 25a and 25b simultaneously firmly clamps the central portion of detent 26 within capture element 25. The greater the downward pulling force on plunger 22 is, the greater the clamping force exerted by capture element arms 25a and 25b. Therefore, capture element 25 can very firmly clamp detent 26 without loosening (as shown in FIG. 9).

As shown in FIGS. 8 and 9, after needle 24 is fully retracted into barrel 21, capture element arms 25a and 25b slightly loosen their grip on detent 26 (once the user stops pulling on plunger 22) so that tip 40 of needle 24 will laterally tilt due to the unstable seating of capture element 25 on detent 26. At this time, tip 40 is positioned under shoulder section 33 of barrel 21. The closed small end 61 of needle sheath 44 originally fitted around needle holder 23 is then inserted into needle holder cavity 31 to seal needle holder cavity 31. Therefore, tip 40 of needle 24 is prevented from unexpectedly protruding out of needle holder cavity 31. Finally, as shown in FIG. 10, plunger 22 is pushed forward to press tip 40 of needle 24 against shoulder 33 of barrel 21 so as to bend and destroy needle 24.

FIGS. 11 to 14 show a second preferred embodiment of the present invention, in which the operation procedure of syringe 20 described above with regard to the first preferred embodiment is identical to that of the second embodiment. Though the principle features of the first preferred embodiment are shared with the second preferred embodiment, a major difference between the two embodiments is that the positions of capture element 25 and detent 26 are exchanged. To insure that the seating of detent 26 in capture element 25 is unstable (thereby resulting in lateral tilting of needle 24 and needle holder 23 when needle 24 is fully retracted into barrel 21), the length of detent 26 may be elongated such that the end of detent 26 rests upon the first end 34 of plunger 22 when detent 26 is captured within capture element 25 and when needle 24 has been fully retracted within barrel 21. To further destabilize the seating of detent 26 in capture element 25, the surface 25c of capture element 25 may be tilted (not shown) with respect to a plane perpendicular to axis 47 of barrel 21.

Also shown in the second preferred embodiment in FIGS. 11–14 (and in FIGS. 15–17) is an alternate form of detent 26. In the second preferred embodiment, detent 26 is split into three parts, permitting detent 26 to flex and collapse as it enters into capture element 25 and then to spring back to its normal split state once fully inserted into capture element 25. In this manner, detent 26 may be inserted into a smaller capture element 25, thereby insuring better capture of detent 26 in capture element 25.

Figures 19, 20, 21:
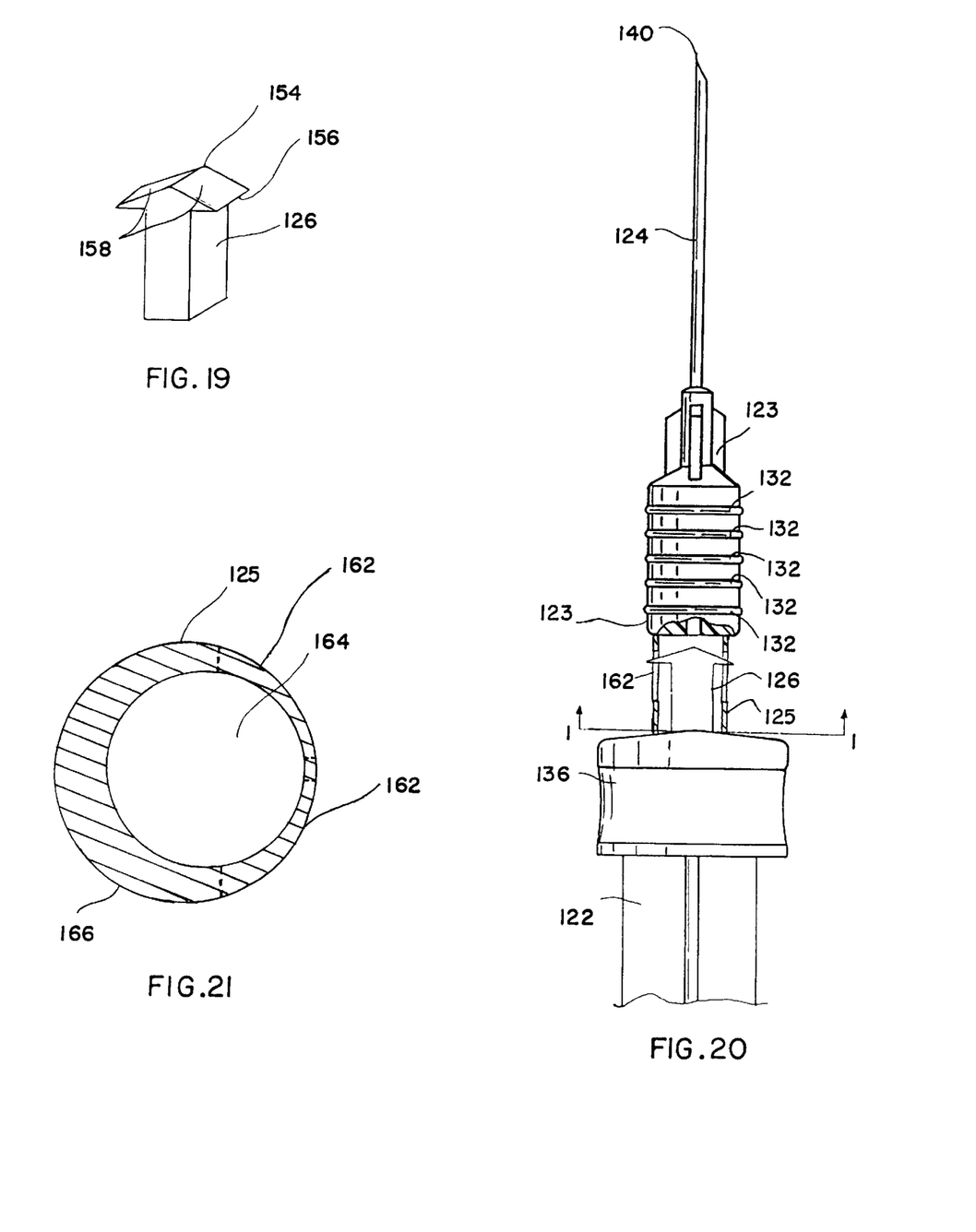
FIG. 19 is a perspective view of the detent of the fourth embodiment.
FIG. 20 is a front view showing the syringe of the fourth embodiment when the liquid medicine is about to be completely injected and the detent is passing through the capture element.
FIG. 21 is a cross-sectional view of the syringe shown in FIG. 20, taken along the line 1—1 in FIG. 20.

As an alternative to the detent 26 and capture element 25 arrangement used in the first and second embodiments discussed above, FIGS. 18–21 show a modified version of detent 126 and capture element 125. In these figures, capture element 125 is an open-ended tubular-shaped member extending from the second end 138 of needle holder 123. The walls 166 of capture element 125 have two windows 162. Though only two windows are shown on one side of capture element 125 in FIGS. 18–21, more or fewer windows in various positions in walls 166 are possible. As best seen in FIG. 19, detent 126 is not round (as in the first and second embodiments), but is rectangular with a tip 154 having two arms 158. As with the detent shown in FIGS. 11–17, detent 126 may be split. In use, detent 126 is pushed toward capture element 125 when plunger 122 is depressed. As detent 126 is pressed into end hole 164 of capture element 125, arms 158 of tip 154 flex to squeeze into end hole 164. As detent 126 is further pressed into end hole 164, arms 158 snap into place in windows 162. In this manner, when plunger 122 is withdrawn, arms 158 in windows 162 pull capture element 125, needle holder 123, and needle 124 into barrel 121 (not shown) as described in the first and second embodiments. As also described in the first and second embodiments, the positions of capture element 125 and detent 126 may be reversed from their positions shown in FIGS. 18–21.

FIG. 21 is a cross-sectional view of capture element 125 taken along lines 1—1 in FIG. 20. As can be seen in FIG. 21, end hole 164 is located within capture element 125 such that walls 166 are not of uniform thickness. Though walls 166 may be of uniform thickness, by locating end hole 164 in a non-concentric location with respect to capture element 125, when detent 126 is pressed into end hole 164, detent 126 is forced to bend along its length. This bending of detent 126 creates an increased pressure of at least one arm 156 against the inside of capture element wall 166, which causes a tighter engagement of the at least one arm 156 into window 162 when arm 156 enters window 162. This tighter engagement insures improved latching of detent 126 to capture element 125.

According to the above arrangement, the present invention has the following advantages:

1. The safety syringe can avoid leakage of liquid medicine and prevents the needle from accidentally becoming disconnected from the barrel. Also, the needle can be easily pulled back into the barrel.
2. The plunger can be easily firmly latched with the needle and the needle can be also reliably pulled back into the barrel.
3. Before the injection is completed, the needle is prevented from being latched by mistake.

It is to be understood that the above description and drawings are only used for illustrating some embodiments of the present invention, and are not intended to limit the scope of the present invention. Any variation and derivation from the above description and drawings should be included in the scope of the present invention.

What is claimed is:

1. A retractable, destructible syringe comprising:
   a syringe barrel having a first end and a second end;
   a plunger having a first end and a second end, the first end of the plunger being fitted within the second end of the syringe barrel;
   a needle holder having a first end, a second end, and an axis, the second end of the needle holder being releasably secured within the first end of the syringe barrel;
   a needle disposed in the first end of the needle holder;
   a needle retracting assembly located between the first end of the plunger and the second end of the needle holder, the needle retracting assembly having:
      a detent; and
      a capture element,
   the detent engaging with the capture element when the plunger is depressed into the syringe barrel, thereby forming a connection between the capture element and the detent, the connection permitting the needle holder and the needle to be retracted into the syringe barrel when the plunger is retracted from the syringe barrel, the connection providing support for the needle holder only in a direction along the axis of the needle holder, thereby permitting the needle and the needle holder to pivot about the connection when the needle is fully withdrawn into the syringe barrel.

2. The retractable destructible syringe as claimed in claim 1, wherein the detent is attached to the first end of the plunger and wherein the capture element is attached to the second end of the needle holder.

3. The retractable destructible syringe as claimed in claim 1, wherein the detent is attached to the second end of the needle holder and wherein the capture element is attached to the first end of the plunger.

4. The retractable destructible syringe as claimed in claim 1, wherein the capture element includes at least two arms, wherein the detent includes a tip and a hook surface, the tip pushing the at least two arms apart as the detent is pressed into the capture element, and wherein the hook surface presses against the at least two arms to prevent retraction of the detent from the capture element once the detent is engaged with the capture element.

5. The retractable destructible syringe as claimed in claim 4, wherein the detent has splits separating the detent into two or more parallel parts.

6. The retractable destructible syringe as claimed in claim 1, wherein the capture element includes an annular wall having at least one window formed therethrough, and wherein the detent includes a tip and at least one arm extending from the tip, the at least one arm of the detent extending into the at least one window when the detent is engaged within the capture element.

7. The retractable destructible syringe as claimed in claim 6, wherein the annular wall has varying thickness along its circumference.

8. The retractable destructible syringe as claimed in claim 1, wherein the first end of the syringe barrel has an interior surface with at least one sealing fixing ring releasably holding the needle holder in place with a fluid-tight seal within the first end of the syringe barrel.

9. The retractable destructible syringe as claimed in claim 1, wherein the second end of the needle holder has an exterior surface with at least one sealing fixing ring, the at least one sealing fixing ring securably holding the needle holder in place with a fluid tight seal within the first end of the syringe barrel.

10. The retractable destructible syringe as claimed in claim 8, wherein the second end of the needle holder has an exterior surface with at least one sealing fixing ring interengaging with the at least one sealing fixing ring on the interior surface of the syringe barrel, the at least one sealing fixing ring on the second end of the needle holder securably holding the needle holder in place with a fluid tight seal within the first end of the syringe barrel.

11. The retractable destructible syringe as claimed in claim 1, further including:
   a latch plate hinged and secured at one end to the second end of the syringe barrel, the latch plate having a first latch section;
   a second latch section secured to the second end of the plunger and adapted to releasably connect to the first latch section, thereby preventing movement of the plunger relative to the barrel.

12. A retractable destructible syringe comprising:
   a needle holder;
   a needle inserted within the needle holder;
   a barrel;
   a plunger inserted within the barrel;
   a needle retracting assembly located between the needle holder and the plunger, the needle retracting assembly having
   a detent; and
   a capture element,
   the detent and the capture element creating a connection between the needle holder and the plunger when the detent is engaged within the capture element, the connection permitting rotation of the needle holder and needle with respect to the plunger.

13. The retractable destructible syringe as claimed in claim 12, wherein the detent is attached to the plunger and wherein the capture element is attached to the needle holder.

14. The retractable destructible syringe as claimed in claim 12, wherein the detent is attached to the needle holder and wherein the capture element is attached to the plunger.

15. The retractable destructible syringe as claimed in claim 12, wherein the capture element includes at least two arms, wherein the detent includes a tip and a hook surface, the tip pushing the at least two arms apart as the detent is pressed into the capture element, and wherein the hook surface presses against the at least two arms to prevent retraction of the detent from the capture element once the detent is engaged with the capture element.

16. The retractable destructible syringe as claimed in claim 15, wherein the detent has splits separating the detent into two or more parts.

17. The retractable destructible syringe as claimed in claim 12, wherein the capture element includes an annular wall having at least one window formed therethrough, and wherein the detent includes a tip and at least one arm extending from the tip, the at least one arm of the detent extending into the at least one window when the detent is engaged within the capture element.

18. The retractable destructible syringe as claimed in claim 17, wherein the annular wall has varying thickness along its circumference.

19. The retractable destructible syringe as claimed in claim 12, wherein at least one sealing fixing ring releasably holds the needle holder in place within the barrel through a fluid-tight seal.

20. A retractable and destructible safety syringe comprising:
   a syringe barrel having a first end and a second end and being formed with an internal chamber, the first end of the syringe barrel being disposed with a needle socket defining a needle holder cavity, an annular shoulder section being formed between the internal chamber and the needle holder cavity;
   a plunger having a first end and a second end, the first end of the plunger being disposed with a piston and fitted into the syringe barrel, the plunger having a first axis;
   a needle holder having a first end and a second end, an outer periphery of the second end of the needle holder being fitted in the needle holder cavity, the needle holder having a second axis;
   a needle inserted into the first end of the needle holder; and
   a needle retracting means including:
   a capture element having a first end and a second end, the first end of the capture element being rotatably disposed on one of either the first end of the plunger or the second end of the needle holder, a distance between the first end of the capture element and either of the first or second axes being defined as a first distance, the second end of the capture element extending toward the other of either the first end of the plunger or the second end of the needle holder, in a free state, a distance between the second end of the capture element and either of the first or second axes being defined as a second distance, the second distance being less than the first distance; and
   a detent having a first end and a second end, the first end of the detent being disposed on the other of either the first end of the plunger or the second end of the needle holder, the first end of the detent extending along the axes toward one of either the first end of the plunger or the second end of the needle holder, the second end of the detent being disposed with a hook section having a radially extending hook surface, whereby when the first end of the plunger is pushed to the first end of the barrel, the hook section of the detent slides over the second end of the capture element and when the plunger is pulled from the first end of the barrel to the second end thereof, the hook surface of the hook section abuts against the second end of the capture element to force the second end of the capture element toward the center of the detent so as to firmly engage with the hook surface of the hook section and to pull the needle holder and the needle back into the barrel.

21. A safety syringe as claimed in claim 20, wherein at least two capture elements are radially arranged about the axes.

22. A safety syringe as claimed in claim 20, wherein said needle holder cavity has at least one inner wall, said one of either the inner wall of the needle holder cavity or the outer periphery of the needle holder further includes a sealing fixing ring.

23. A safety syringe as claimed in claim 22, wherein at least two sealing fixing rings are provided.

24. A safety syringe as claimed in claim 20, wherein both the inner wall of the needle holder cavity and the outer periphery of the needle holder further includes sealing fixing rings fitted with each other.

25. A safety syringe as claimed in claim 20, wherein at least two sealing fixing rings are provided.

26. A safety syringe as claimed in claim 20, further comprising:
   a latch plate having a first end and a second end, the first end of the latch plate being connected with the second end of the barrel;
   a first latch section disposed at the second end of the latch plate; and
   a second latch section disposed at the second end of the plunger, the second latch section being latched with the first latch section so as to locate the detent near the capture element and to prevent the detent from engaging with the capture element by mistake.

* * * * *